(12) United States Patent
Han et al.

(10) Patent No.: US 6,653,092 B2
(45) Date of Patent: Nov. 25, 2003

(54) METHOD TO DETERMINE HYDROGEN PEROXIDE

(75) Inventors: Qinghong Han, San Diego, CA (US); Li Tang, San Diego, CA (US); Mingxu Xu, San Diego, CA (US); Yuying Tan, San Diego, CA (US); Shigeo Yagi, San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 1 day.

(21) Appl. No.: 10/003,597

(22) Filed: Oct. 30, 2001

(65) Prior Publication Data

US 2002/0037545 A1 Mar. 28, 2002

Related U.S. Application Data

(62) Division of application No. 09/550,723, filed on Apr. 17, 2000, now Pat. No. 6,329,162.
(60) Provisional application No. 60/129,730, filed on Apr. 16, 1999.

(51) Int. Cl.[7] .................................................. C12Q 1/48
(52) U.S. Cl. .............................. 435/15; 435/4; 564/305
(58) Field of Search ......................... 435/15, 4; 564/305

(56) References Cited

U.S. PATENT DOCUMENTS 5,182,213 A * 1/1993 Genshaw et al. ............. 436/66
6,046,017 A * 4/2000 Schirch ........................ 435/25
6,329,162 B1 * 12/2001 Han et al. ..................... 435/15
6,448,446 B1 * 9/2002 Tang et al. .................. 564/437

OTHER PUBLICATIONS

Ohtsuki E. Colirimetric Determination of Urinary Xanthurenic Acid Using an Oxidative Coupling Reaction with N,N–Diethyl–p–phenylenediamine. Biol Pharm Bull 17(1)139–141,1994.*
Isachenkov V. The Use of Color Photography Reagents in Analyses Based on the Detection of Peroxidase Reactions. Russian Biotechnology No. 6, pp. 18–24, 1995.*
Ogawa et al. J Biol Chem 257(7):3447–3452 3(1982).
Sanghani et al. Protein Expression and Purification 18:36–45 (2000).
Santos et al. Electrophoresis 16:1898–1899 (1995).
Wagner et al. Biochem Biophys Res Communs 127(3):746–752 (1985).
Yeo et al. J Biol Chem 267(34):24669–24674 (1992).
Yeo et al. J Biol Chem 274(53):37559–37564 (1999).

* cited by examiner

*Primary Examiner*—Ralph Gitomer
(74) *Attorney, Agent, or Firm*—Morrison & Foerster LLP

(57) ABSTRACT

A method to detect and measure the concentration of hydrogen peroxide comprises adding reagents consisting essentially of peroxidase and a dialkyl phenylenediamine and detecting any color generated by the interaction of hydrogen peroxide with these reagents.

8 Claims, No Drawings

METHOD TO DETERMINE HYDROGEN PEROXIDE

This application is a divisional of U.S. Ser. No. 09/550,723 filed Apr. 17, 2000, now U.S. Pat. No. 6,329,162 which claims priority under 35 United States Code §119(e) from provisional application Ser. No. 60/129,730 filed Apr. 16, 1999. The contents of these applications are incorporated herein by reference.

TECHNICAL FIELD

The invention relates to diagnostic methods for conditions which are characterized by abnormal levels of certain metabolites, in particular, folates, and to simplified methods of detection. The improved methods of the invention provide rapid and accurate assessment of the concentrations of folate and other analytes.

BACKGROUND ART

Folates are critical co-factors in methyl transfer reactions. Abnormalities of folate levels in biological fluids such as blood and plasma are indicative of conditions that are characterized by inappropriate or inadequate transfer of methyl groups. Thus, it is important to be able to provide an accurate measure of folate levels in such fluids and to compare them to those expected in normal individuals. Low folate concentrations are associated with megaloblastic anemia and reduced DNA synthesis, as well as cardiovascular disease. Birth defects may also result.

Folate can be measured efficiently using the methods of the invention. The invention also provides an improved method to detect $H_2O_2$ in the presence of peroxidase

DISCLOSURE OF THE INVENTION

The invention method for determining levels of folate in biological fluids takes advantage of the ability of folate to inhibit the methyl transfer reaction whereby glycine is converted to sarcosine. The enzyme which carries out this conversion, glycine N-methyltransferase (GMT) can be isolated from liver or pancreas. In the assay systems of the invention, glycine and S-adenosyl methionine (SAM) are the reactants and sarcosine and S-adenosyl homocysteine (SAH) are the products. The effectiveness of GMT in converting these reactants is dependent on folate concentration in vivo.

The folate in the sample can be converted to a form (to the extent it does already exist in said form) whereby it inhibits the ability of GMT to form the foregoing products. The folate in the sample is first converted to folypoly glutamate (FPG) which is an inhibitor of the GMT. Yeo, E-J, et al., *J. Biol. Chem.* (1999) 274:37556–37564. Under these conditions, the greater the amount of folate in the sample, the less products formed.

In the invention method, the levels of product are typically measured. As the levels of reactants are provided in excess, although it is theoretically possible to measure the diminution in reactants, this is less desirable as it is, of course, more difficult to detect small differences in large concentrations than to measure a difference from zero. However, it is not impossible, and such measurements are within the scope of the invention as well.

Either the levels of SAH or of sarcosine can be measured or both. A variety of methods is available in each case. Preferred embodiments for the measurement of SAH, however, include its conversion to homocysteine and subsequent lysis of homocysteine to obtain readily detectable products as further described below. In the case of sarcosine, a convenient method is the use of a specific oxidase which, in the presence of this amino acid, generates hydrogen peroxide which can also be readily detected by a variety of methods known in the art, preferred embodiments of which are illustrated below. Thus, in one aspect, the invention is directed to:

A method to assess the level of folate in a biological fluid sample which method comprises
  providing said sample with glycine N-methyltransferase (GMT) and with an excess of S-adenosyl methionine (SAM) and of glycine;
  providing a control which contains no folate with said GMT and excess SAM and glycine in comparable amounts to those provided to the sample; and
  comparing the concentration of at least one product formed in the sample with the concentrations of said product formed in the control,
  whereby the difference in levels of said product in the sample as compared to the control is directly proportional to the level of folate in the sample.

In the foregoing method, either sarcosine or SAH levels may be measured. The concentrations of products will be diminished in the sample as compared to the control. Pretreatment of the sample with an enzyme which converts folate to an inhibitor of GMT, FPG, set forth above, is desirable. This enzyme, folypoly glutamate synthetase (FPGS) is readily available in the art.

In another aspect, the invention is directed to a particularly convenient method for the endpoint of sarcosine measurement. It has been found that a particularly convenient method to measure hydrogen peroxide in analytical samples, including biological fluids, is to treat the sample containing the peroxide with both peroxidase and a dialkyl phenylene diamine. The resultant is a colored compound which can be measured spectrophotometrically. As will be evident, since a number of protocols are available which result in the generation of hydrogen peroxide, for example the treatment of substrates with their pertinent corresponding and specific oxidases, the combination of peroxidase and dialkyl phenylene diamines has a broad range of utility.

MODES OF CARRYING OUT THE INVENTION

The invention is directed, in one embodiment, to the measurement of folates in biological fluids. Suitable biological fluids are most commonly blood, serum and plasma, although other fluids may be of interest as well, such as cerebral spinal fluid, urine, and other blood fractions. Measurement in plasma or serum is preferred.

By "folates" is meant folic acid and its salts as well as the dihydro and teterahydro form. In order to ensure uniformity of results, it may be desirable to add a reducing agent to the reaction mixtures in order to ensure that all of the folates are in the same oxidation state—i.e., the teterahydro folate (THF) form. However, it is believed that the predominant form, almost to the exclusion of the others, is biological systems is tetrahydrofolate, and in particular, 5-methyltetrahydrofolate. It is this form, specifically, in combination with glutamate which acts as an inhibitor of GMT endogenously.

By way of background, it is believed that the function of GMT in the liver and pancreas is to diminish undesirably high concentrations of SAM by creating a "sink" in the form of sarcosine, which has no known function. However, this enzyme is regulated by folate; when high levels of methylated THF are present, combination with glutamate occurs and the resulting compound is a powerful GMT inhibitor. The present invention takes advantage of the ability of folates to inhibit GMT using this mechanism.

For use in the present invention, GMT can be isolated from pancreas or liver or theoretically could be produced recombinantly. If the enzyme is isolated from native sources, it should first be treated to disassociate it from any endogenous folate. This can be effected by treating the enzyme with an anion exchange column and effecting a separation using, for example, a gel exclusion method.

In the methods of the invention, glycine N-methyltransferase (GMT) catalyzes the reaction:

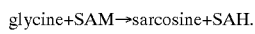

glycine+SAM→sarcosine+SAH.

The GMT is purified from any convenient source. A method for purification of the enzyme from rat liver is described in the examples below; also described is a method to obtain the enzyme free of inhibitor by treating the isolated GMT on an anion exchange column and separating the dissociated folate by gel filtration.

To carry out the method, both control and sample are incubated with folate-free GMT after treatment with glutamic acid in the presence of the enzyme FPGS which converts any folate into an inhibitor of GMT, FPG. Either sarcosine or SAH can be measured, the amounts or concentrations of product present in the sample will be less than those of the control in a degree proportional to the concentration of folate in the sample.

Thus, the sample and the control are treated with glutamine and the synthetase FPGS to convert the folate to an inhibitor (FPG) of the GMT. In this embodiment, the sample is incubated with the glutamine and FPGS in suitable amounts prior to or concomitant with, treatment with GMT. The remainder of the assay is conducted according to the alternatives outlined below. Measurement of SAH or sarcosine provides a measure of the GMT activity which is, in turn, inversely proportional to the level of inhibitor, and thus inversely proportional to the level of folate in the sample.

Detection of SAH

In a preferred method for detection of SAH, the reaction mixtures are treated with S-adenosyl homocysteinase (SAHase) which converts SAH to homocysteine. Homocysteine can then be measured by any method convenient in the art. However, a particularly preferred embodiment employs a recombinant homocysteinase (HCYase), preferably HYase™, which is especially specific for homocysteine. This enzyme is described in detail in PCT publication No. WO99/05311 published Feb. 4, 1999, and incorporated by reference. The use of this particular HYase™ homocysteinase has the advantage of substantially and essentially eliminating any background products which might be formed from methionine or cysteine present in the sample. The products of homocysteine catalysis by this enzyme are ammonia, hydrogen sulfide, and α ketobutyrate. Any of these products may be measured, but it is most convenient to measure the hydrogen sulfide by the use of an oxidizing agent in the presence of any dialkyl phenylene diamine, most conveniently the di-N-butyl embodiment, DBPDA. The complex that is formed between hydrogen sulfide and the dialkyl phenylene diamine in the presence of an oxidizing agent is both chromogenic and fluorescent, and either property can be used for detection. Use of the fluorescence property appears slightly more sensitive.

Thus, in one preferred embodiment, the reaction mixture is treated with SAHase and recombinant homocysteinase HYase and with the chromogen DBPDA and an oxidizing agent such as ferric ion. Either the absorbance at about 675 nm or the fluorescence upon excitation at about 665 nm and emission at 690 nm is measured.

Measurement of Sarcosine

The levels of sarcosine product can conveniently be measured by use of sarcosine-specific enzymes. A particularly preferred sarcosine-specific enzyme is sarcosine oxidase Santos, F., et al., *Electrophoresis* (1995) 16:1898–1899, which generates hydrogen peroxide. Dialkyl phenylene diamines are also chromogenic in the presence of hydrogen peroxide upon breakdown with peroxidase; alternatively, a colored product can be obtained using other reagents, such as 4-chloro-1-naphthol and ortho-toluidine.

Measurement of Peroxide

The are many biological reactions, especially oxidase reactions, which are specific for individual substrates and which result in the production of hydrogen peroxide. Another aspect of the invention is an improved method to measure the concentration of hydrogen peroxide which method comprises adding to the sample where in the peroxide is to be measured both peroxidase, such as horseradish peroxidase, and a dialkyl phenylene diamine. A preferred compound is DBPDA. Illustrative amounts of these reagents are described in the examples below.

The product of the reaction can be measured spectrophotometrically. Alternatively, a fluorescent product is formed which can be detected accordingly.

The following examples illustrate but do not limit the invention.

Preparation A

Purification of Rat Liver Glycine N-Methyltransferase (GMT)

The method is a modified form of that described by Ogawa, H., *J. Biol. Chem.* (1982) 257: 3447–3452; Yeo, E.J., *J. Biol. Chem.* (1992) 267: 24669–24674.

Rats were killed by decapitation and the livers quickly removed and chilled on ice. About 400 g liver was homogenized in a blender with 1.2 l. of 10 mM buffer, pH 7.2, containing 1 mM EDTA. After adjusting to pH 5.5 by dropwise addition of 1.0 M sodium acetate, the precipitate was removed by centrifugation at 10,000×g for 15 min. The clear supernatant solution was recovered and adjusted to pH 7 with 2 N KOH.

The supernatant was made 1% ammonium sulfate and the mixture was allowed to stand for 30 min. with gentle stirring. After centrifugation at 10,000 g for 30 min, the supernatant was recovered and treated with 8 g of ammonium sulfate per 100 ml of supernatant. After 30 min, the mixture was centrifuged as above, and the pellet was recovered, dissolved and dialyzed overnight.

The dialyzed enzyme preparation was divided into equal parts and each was put onto a column of DEAE-Sepharose (5×25 cm) equilibrated with 10 mM buffer, pH 7.2, containing 1 mM EDTA. The pass-through fractions were combined and ammonium sulfate added at 30 g/100 ml. After standing overnight, the pellet was collected by centrifugation and dissolved in buffer.

The enzyme solution containing 1.0 M ammonium sulfate was applied to a Phenyl Sepharose 6 FF (5×25 cm) column prewashed with 10 mM buffer, pH 7.2, containing 1.0 M ammonium sulfate. The bound GMT protein was eluted in a linear gradient of decreasing the ammonium sulfate concentration, using 10 mM buffer, pH 7.2. The peak showing the activity was collected and dialyzed overnight.

Preparation B

Preparation of Apo GMT

Folate was removed from the GMT prepared as in Preparation A. The enzyme solution prepared in Preparation A was passed over and anion exchange column to dissociate the folate ligand, followed by centrifugal gel exclusion using standard methods.

Preparation C

Preparation of the Inhibitor FPG

FPG was prepared from serum or from standard 5-methyltetrahydrofolate solutions by treating with recombinant human FPGS (Paresh, C., *Protein Exp & Pur* (2000) 18:36–45. Serum or 5-methylTHF was incubated with 3 mg purified recombinant human FPGS (0.1 $\mu$M) in the presence of 15 mM glutarnic acid, 10 mM $MgCl_2$, 5 mM ATP, 20 mM KCl, 100 mM $\beta$-mercaptoethanol, 250 $\mu$g BSA, 100 mM Tris-HCl, pH 8.7, in a total volume of 500 $\mu$l at 37° C. for 1.0 hour.

EXAMPLE 1

Determination of Folate by Inhibition of GMT by FPG

GMT (0.95 $\mu$g) as prepared in Preparation A was treated to associate with FPG in a reaction mixture of standard (1–100 nM FPG) or test serum sample containing 20 mM Tris-HCl, pH 9.0 and 5 mM DTT. Various dilutions of Preparation C (FPG prepared from standard methylTHF or from serum) were included in an 800 $\mu$l reaction mixture which was incubated for 15 min. at 25° C.

After the GMT and FPG (either standards or derived from serum) were allowed to associate, the volume was brought in each sample to 1000 $\mu$l with 100 $\mu$l 5 mM glycine and 100 $\mu$l 1 mM SAM. This reaction system also included the assay mixture of 10 $\mu$l recombinant SAHase (2.0 units/ml) and recombinant HYase (300 units/ml). It was incubated at 37° C. for 30 min. During this period, any SAH product is converted to homocysteine and then to hydrogen sulfide, ammonia and pyruvate.

After the 30 min. incubation, 50 $\mu$l 40 mM DBPA and 40 mM $K_3Fe(CN)_6$ were added and the reaction mixture was incubated at 37° C. for 10 min. and read at 675 nm.

EXAMPLE 2

Alternate Assessment Method

A. Assessment of folate in serum was carried out as set forth in Example 1 except that instead of including SAHase and HCYase in the reaction mixture, the reaction system contains 10 $\mu$l sarcosine oxidase (SOX) (4 mg/ml) peroxidase (2 mg/ml) and 10 $\mu$l of 4-chloro-1-naphthol (2% W/V in diethylene glycol) and 20 $\mu$l of o-toluidine (saturated solution in 7% acetic acid). The incubation was again at 37° C. and the optical density was read.

B. The assay of paragraph A was carried out except that no 4-chloro-1-naphthol or o-toluidine were added to the reaction mixture. Instead, 5 mM DBPDA was included, and the optical density read at 558 nm at the end of the 30 min. incubation.

What is claimed is:

1. A method to detect the presence or amount of hydrogen peroxide generated by an analyte in a biological sample, which method comprises contacting said sample with reagents consisting essentially of a peroxidase and a dialkyl phenylenediamine, whereby a color is produced in the sample in the presence of hydrogen peroxide, and detecting the presence or amount of said color, wherein the presence or amount of said color indicates the presence or amount of hydrogen peroxide.

2. The method of claim 1 wherein said dialkyl phenylenediamine is di-n-butyl phenylenediamine (DBPDA).

3. The method of claim 1 wherein said peroxidase is horseradish peroxidase.

4. The method of claim 1 wherein said detecting is performed spectrophotometrically.

5. A method to detect the presence or amount of hydrogen peroxide in a sample which method comprises contacting said sample with reagents consisting essentially of peroxidase and a dialkyl phenylenediamine, whereby a color is produced in the sample in the presence of hydrogen peroxide, and detecting the presence or amount of said color, wherein the presence or amount of said color indicates the presence or amount of hydrogen peroxide.

6. The method of claim 5 wherein said dialkyl phenylenediamine is di-n-butyl phenylenediamine (DBPDA).

7. The method of claim 5 wherein said detecting is performed spectrophotometrically.

8. The method of claim 5 wherein said peroxidase is horseradish peroxidase.

\* \* \* \* \*